United States Patent
Tang et al.

(10) Patent No.: US 9,714,254 B2
(45) Date of Patent: Jul. 25, 2017

(54) ANILINO PODOPHYLLIN DERIVATIVE HAVING ANTITUMOR ACTIVITY, METHOD FOR PREPARATION THEREOF, AND USE THEREOF

(71) Applicant: HUBEI UNIVERSITY OF TECHNOLOGY, Wuhan, Hubei (CN)

(72) Inventors: Yajie Tang, Wuhan (CN); Yong Yang, Wuhan (CN); Wei Zhao, Wuhan (CN); Hongmei Li, Wuhan (CN)

(73) Assignee: HUBEI UNIVERSITY OF TECHNOLOGY, Wuhan (CN)

( * ) Notice: Subject to any disclaimer, the term of this patent is extended or adjusted under 35 U.S.C. 154(b) by 0 days.

(21) Appl. No.: 15/036,673

(22) PCT Filed: Sep. 5, 2014

(86) PCT No.: PCT/CN2014/085995
§ 371 (c)(1),
(2) Date: May 13, 2016

(87) PCT Pub. No.: WO2015/070662
PCT Pub. Date: May 21, 2015

(65) Prior Publication Data
US 2016/0289242 A1 Oct. 6, 2016

(30) Foreign Application Priority Data
Nov. 15, 2013 (CN) .......................... 2013 1 0571026

(51) Int. Cl.
*A01N 43/26* (2006.01)
*A61K 31/335* (2006.01)
*C07D 493/04* (2006.01)
*A61K 31/365* (2006.01)

(52) U.S. Cl.
CPC .......... *C07D 493/04* (2013.01); *A61K 31/365* (2013.01); *Y02P 20/582* (2015.11)

(58) Field of Classification Search
None
See application file for complete search history.

(56) References Cited

U.S. PATENT DOCUMENTS 5,536,847 A 7/1996 Terada et al.

FOREIGN PATENT DOCUMENTS

| CN | 1064278 A | 9/1992 |
|----|-----------|--------|
| CN | 1563011 A | 1/2005 |
| CN | 102875564 A | 1/2013 |
| CN | 103601732 A | 2/2014 |

OTHER PUBLICATIONS

Kamal et al. (Bioorganic & Medicinal Chemistry Letters, 10, 2059-2062, 2000).*
International Search Report for PCT/CN2014/085995 mailed on Dec. 9, 2014.
Kamal et al., "Facile and Efficient One-Pot Synthesis of 4β-Arylamino-podophyllotoxins: Synthesis of DNA Topoisomerase II Inhibitors (NPF and W-68)", Bioorganic & Medicinal Chemistry Letters 10 (2000), pp. 2059-2062.
Liu et al., "Synthesis and insecticidal activities of novel derivatives of podophyllotoxin", Natural Product Research, vol. 21, No. 11, Sep. 2007, pp. 967-974.

* cited by examiner

*Primary Examiner* — Dennis Heyer
*Assistant Examiner* — Daniel M Podgorski
(74) *Attorney, Agent, or Firm* — Birch, Stewart, Kolasch & Birch, LLP

(57) ABSTRACT

The present invention discloses an anilino-substituted podophyllin derivative having antitumor activity, method for preparation thereof, and use thereof. By means of anilino reactions, the present invention introduces 4-chloro-3-methylaniline, 3-fluoro-4-methoxyaniline, 4,4'-diaminodiphenylmethane, o-anisidine, 4-chloro-2-aminoanisole, anthranilonitrile, 2,6-dichloro-4-aminophenol, N,N-dimethylamino meta-aniline, 2-ethyl-5-nitroaniline, 2 2'-diaminodiphenylsulfide, or 2-aminobenzotrifluoride into position 4 of the active C-ring of podophyllotoxin or 4'-demethylepipodophyllotoxin to obtain the aniline-substituted podophyllotoxin derivative shown in formula (V); by means of multi-pathway and multi-target effects on tumor cells, said derivative has significantly increased antitumor activity, and can be prepared as an antineoplastic drug and applied in clinical antitumor therapy.

9 Claims, 3 Drawing Sheets formula(V)

(Podophyllotoxin)      (4'-Demethylepipodophyllotoxin)

formula(I)             formula(II)

4-Chloro-3-methylaniline  3-Fluoro-4-methoxyaniline  4,4'-Diaminodiphenylmethane  o-Anisidine 5-Chloro-2-methoxyaniline  2-Amino-5-nitrobenzonitrile  4-Amino-2,6-dichlorophenol  N,N-Dimethyl-m-phenylenediamine 2-Ethyl-5-nitrobenzenamine  2,2-Diaminophenylsulfide  2-(Trifluoromethyl)aniline

ANILINO PODOPHYLLIN DERIVATIVE HAVING ANTITUMOR ACTIVITY, METHOD FOR PREPARATION THEREOF, AND USE THEREOF

TECHNICAL FIELD OF THE INVENTION

Embodiments of the present invention relate to podophyllotoxin-type derivatives, mainly related to aniline-substituted podophyllotoxin-type derivatives after substituting position 4 of the C-ring of 4'-demethylepipodophyllotoxin or podophyllotoxin, and preparation method thereof. Embodiments of the present the invention also relate to use of aniline-substituted podophyllotoxin-type derivatives in the preparation of anti-tumor drugs, belonging to field of preparation and application of podophyllotoxin-type derivatives.

BACKGROUND OF THE INVENTION

Podophyllotoxin and 4'-demethylepipodophyllotoxin are precursor compounds with unique anti-tumor natural activity, extracted from podophylloideae plants (such as Berberidaceae Sinopodophyllum hexandrum, umbrellaleaf, dysosma versipellis etc.). However, podophyllotoxin or 4'-demethylepipodophyllotoxin has more or less shortcomings to be overcome, such as strong toxic and side effect and poor bioavailability, thus limiting their clinical application.

SUMMARY OF THE INVENTION

One purpose of embodiments of the present invention is to provide a kind of aniline-substituted podophyllotoxin-type derivatives with anti-tumor activity;

Second purpose is to provide a method for preparing or purifying the aniline-substituted podophyllotoxin derivatives;

Third purpose is to apply the aniline-substituted podophyllotoxin derivatives and salts thereof to the preparations of the clinical anti-tumor drugs.

The purposes as above are realized by the following technical scheme:

Structural formula of aniline-substituted podophyllotoxin-type derivatives with anti-tumor activity are illustrated on formula (V):

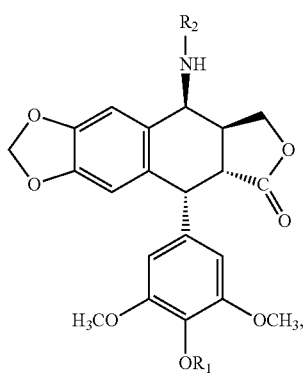

formula (V)

wherein R1 is hydrogen or methyl;
R2 is selected from

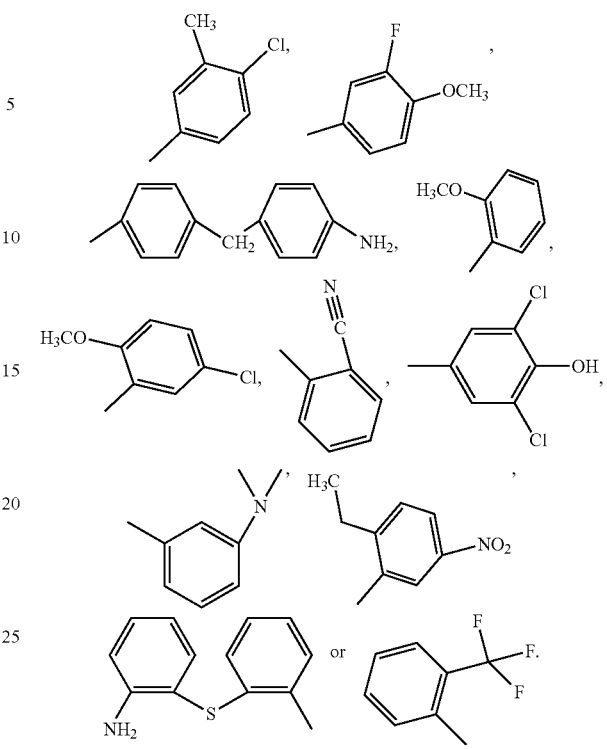

In addition, of course, acid salts of compounds of formula (V) are also included in the scope of embodiments of the present invention. Preferably, the acid salts include hydrochloride, phosphate, and so on.

Anilines are a pharmaceutical intermediates of antineoplastic drugs in which benzene ring is capable of generating π-π bond with biological macromolecules, and these compounds with benzene ring contain active atoms such as chlorine, nitrogen, sulfur, which can enhance binding capacity of the compounds with tubulin or topoisomerase II, making it act on active sites of tubulin and topoisomerase II better, so that the drug's anti-tumor activity increased. With embodiment of the present invention, based on the principle of drug combination, taking these compounds as derivatives of nucleus, taking 4'-demethylepipodophyllotoxin and 4-chloro-3-methylaniline, 3-fluoro-4-methoxyaniline, 4,4'-diaminodiphenylmethane, o-anisidine, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide, or 2-aminobenzotrifluoride as functional groups modified from structure of podophyllotoxin or 4'-demethylepipodophyllotoxin, which are introduced into position 4 of C-ring of podophyllotoxin and 4'-demethylepipodophyllotoxin, to get the compound as shown in formula (V) in embodiment of the present invention.

The second purpose is to provide a method for preparing the above compound of above formula (V), which is comprising the steps of: by aniline reaction, 4-chloro-3-methylaniline, 3-fluoro-4-methoxyaniline, 4,4'-diaminodiphenylmethane, o-anisidine, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide or 2-aminobenzotrifluoride is introduced into position 4 of C-ring of podophyllotoxin and 4'-demethylepipodophyllotoxin, to get the compound as shown in formula (V).

The aniline reaction is preferably carried out under conditions as below: (1) position 4 of C-ring of podophyllotoxin or 4'-demethylepipodophyllotoxin is activated; (2) podophyllotoxin or 4'-demethylepipodophyllotoxin with activated position 4 of C-ring is dissolved in organic solvent, then added 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide or 2-aminobenzotrifluoride, stirred to carried out aniline reaction.

Wherein manner of activation of position 4 of C-ring of podophyllotoxin and 4'-demethylepipodophyllotoxin is to use hydrobromic acid to activate position 4 of C-ring of podophyllotoxin and 4'-demethylepipodophyllotoxin; more preferably, the manner of activation include the steps of: podophyllotoxin and 4'-demethylepipodophyllotoxin being dried, and under protection of nitrogen, hydrobromic acid being added while stirring under ice-bath; after the addition, ice-bath is removed, then reacting under 20-25° C. for 5-12 hours.

The organic solvent in step (2) is preferably methylene chloride.

To achieve better synthesis effect, in aniline reaction, molar ratio between podophyllotoxin or 4'-demethylepipodophyllotoxin and 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide or 2-aminobenzotrifluoride is preferably 1:2.

Stirring in step (2) is preferably such a stirring in vacuo with preferred rotational speed of 50 to 800 rpm, more preferred 600 rpm. Temperature of the aniline reaction is preferably 80° C., reaction time is preferably 12-48 hours, more preferably 48 hours.

In order to achieve better technical effect, above reaction product can be subjected to preliminary purification under the following conditions to get preliminarily purified anilino podophyllotoxin-type derivative as product: anilino podophyllotoxin-type as crude product is subjected rotary evaporation and concentration, then extracted by methylene chloride and water with volume ratio of 1:1 three times, then organic layer is collected, and dried in vacuo to get the preliminarily purified anilino podophyllotoxin-type derivative as product.

The embodiment of present invention also provides a method of further purification of the preliminarily purified aniline-substituted podophyllotoxin-type derivative as product, comprising:

(1) preparation of sample to be separated and purified: preliminarily purified anilino-substituted podophyllotoxin-type derivative as product being extracted by methylene chloride and water with volume ratio of 1:1 three times, and dried in vacuo after organic layer is collected, to be use later;

(2) separation and purification: sample prepared in step (1) being subjected to silica gel column chromatography and gel column chromatography separations sequentially, to obtain product;

Preferably, separation method by silica gel column chromatography comprises: (1) the silica gel column chromatography being normal phase silica gel column chromatography, wherein normal phase silica gel is mixed in organic solvent with low polarity, loaded into column, balanced with eluent which is preferably formed from chloroform and acetone with volume ratio of 10:1; (2) samples being dissolved with the eluent, subjected to sample adsorption, then eluted with eluent which is collected later, then the sample being evaporated to dryness and recrystallized;

Preferably, separation method by gel column chromatography comprises: (1) soaking the gel in methanol; loading processed gel into column and balanced with methanol; (2) sample preliminary separated by silica gel column chromatography being dissolved in methanol, subjected to sample absorption, and then eluated with eluent which is collected later, then the sample being evaporated to dryness and recrystallized;

According to embodiments of the present invention, podophyllotoxin or 4'-demethylepipodophyllotoxin and 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide or 2-aminobenzotrifluoride are subjected to aniline reaction, to get the compound of formula (V) with good anti-tumor activity, which can act on tumor cells by multi-path, multi-target point, thereby achieving better anti-tumor efficacy. In vitro BGC823, Hela, A549 cells activity inhibition tests show that the compound of formula (V) of embodiment of the invention has significantly better antitumor activity than podophyllotoxin or 4'-demethylepipodophyllotoxin. Result of the test indicates that the compound of formula (V) can be used to prepare anticancer drugs, which can be clinically applied to anti-tumor therapy.

Another object of embodiment of the present invention is to provide a kind of pharmaceutical composition, which is formed from combination of the compound of the formula (V) and a pharmaceutically acceptable carrier, that is, after combining of compound of the formula (V) with pharmaceutically acceptable amount and the pharmaceutically acceptable carrier, according to conventional preparing methods in the art, it can be used to preparing any kind of suitable pharmaceutical composition, e.g., which may be in the form of tablets, capsules, powders, granules, pastilles, suppositories, or a liquid form of oral or sterile parenteral suspensions and the like, may also be form of large or small volume of injection, freeze-dried powder, sterile powder dispensing and the like. Typically, the pharmaceutical composition is suitable for oral administration and injection administration, is also suitable for other methods of administration, such as transdermal administration.

In order to achieve consistency of administration, the pharmaceutical composition of embodiment of the present invention is preferably in a form of single agent. Form of single agent for oral administration may be tablets and capsules, and may contain conventional excipients such as binders, e.g., syrup, acacia, gelatin, sorbitol, tragacanth, or polyvinylpyrrolidone; fillers, e.g., lactose, sugar, maize-starch, calcium phosphate, sorbitol or glycine; tabletting lubricants, e.g., magnesium stearate; disintegrants, e.g., starch, polyvinylpyrrolidone, sodium starch glycollate or microcrystalline cellulose, or a pharmaceutically acceptable wetting agents, such as sodium lauryl sulfate.

DETAILED DESCRIPTION OF THE INVENTION

Figure 1:
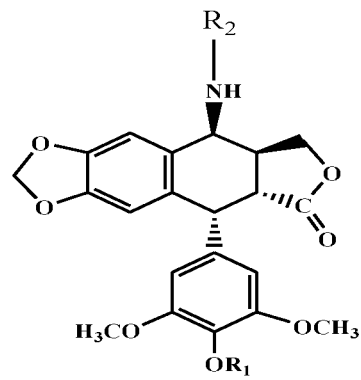
FIG. 1 shows result of general formula of aniline-substituted podophyllotoxin-type derivatives according to embodiment of the invention.
Figure 2:
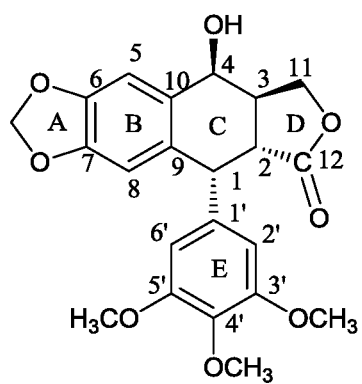
FIG. 2 shows structural formula of podophyllotoxin and 4'-demethylepipodophyllotoxin.
Figure 2:
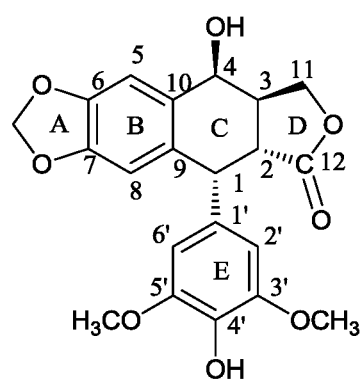
Figure 3:
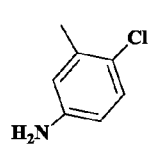
FIG. 3 shows structural formula of 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide or 2-aminobenzotrifluoride.
Figure 3:
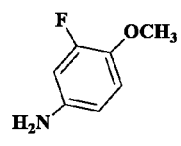
Figure 3:
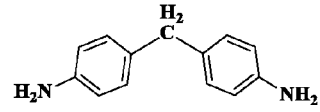
Figure 3:
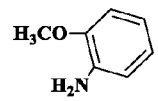
Figure 3:
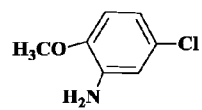
Figure 3:
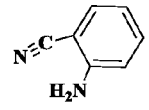
Figure 3:
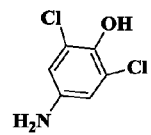
Figure 3:
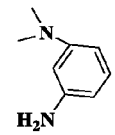
Figure 3:
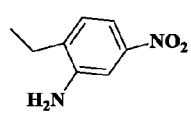
Figure 3:
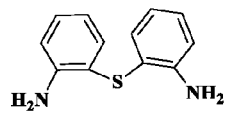
Figure 3:
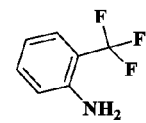
Figure 4:
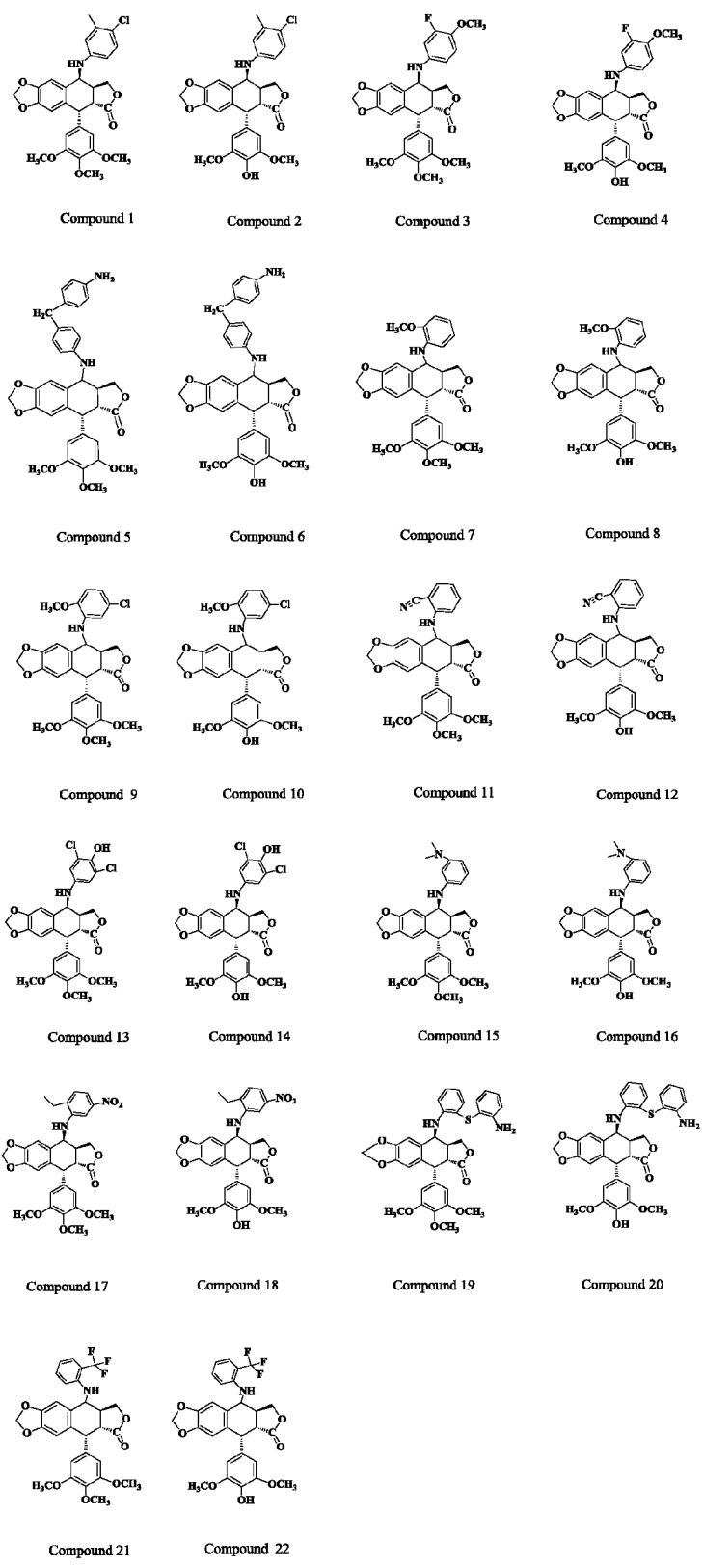
FIG. 4 shows chemical structural formula of 22 aniline podophyllotoxin-type derivatives.

For a fuller understanding of the nature and advantages of the present invention, reference should be made to the ensuing detailed description and the accompanying drawings. Other aspects, objects and advantages of the invention will be apparent from the drawings and the detailed description that follows. it should be noted that, the above embodiments are used to explain the technical solution of the present invention and the present invention should not be construed as being limited to such embodiments, although the present invention has been described in detail with reference to preferred embodiments thereof, it will be understood by those of ordinary skill in the art that various changes or equative replacements may be made to the technical solution of the present invention without departing from the spirit and scope of the present invention as defined by the following claims.

Test Material podophyllotoxin and 4'-demethylepipodophyllotoxin: bought from Xi'an Helin Bio-technique Co., Ltd, with purity of 98%; 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2 2'-diaminodiphenylsulfide or 2-aminobenzotrifluoride, bought from Aladdin reagents.

Preparatory Test Example 1: Activation of Position 4 of C-Ring of Podophyllotoxin and 4'-Demethylepipodophyllotoxin Drying of dichloromethane: taking 1.5 g of calcium hydride to 1000 ML 4-neck flask with round bottom; putting clean funnel into side open thereof; pouring 500 ML of dichloromethane; adding 3-4 glass beads to prevent bumping, heated to the temperature of slightly boiling state of dichloromethane, added to reflux pipe to reflow for 2-3 h, then condensed and collected to reagent bottle containing anhydrous calcium chloride; after that, inputting a little nitrogen to the bottle, closing lid thereof; after each use, nitrogen will be supplemented.

Taking 2 g of podophyllotoxin or 4'-demethylepipodophyllotoxin, which is dried in vacuo at 45° C. for 2 hours; under protection of nitrogen, dried podophyllotoxin or 4'-demethylepipodophyllotoxin and 40 ml of dried dichloromethane were added into 250 ml 4-necked flask, cooled with ice-bath to 0° C., stirred and slowly dropwise added with 5.4 ml of hydrobromic acid; after the addition, ice-bath is removed, then reacting under 25° C. for 5-12 hours. After completion of the reaction, reaction solution is extracted with 20 ml of water, and the lower layer organic phase was taken and repeatedly extracted with saturated aqueous sodium chloride solution three times; and the organic phase is taken and dried in anhydrous sodium sulfate for a night; taking supernatant to be dried by rotary evaporation, then adding 20 ml of ethyl acetate to be dissolved; after that, n-hexane is slowly added dropwise to the solution which then is shaken until no crystals were precipitated, overnighted at 4° C., then crystals are separated from the liquid, resulting compound is activated product of position 4 of C-ring of podophyllotoxin or 4'-demethylepipodophyllotoxin.

Embodiment 1: synthesis and purification of 4-N-(4-chloro-3-methylaniline)-4-deoxy-podophyllotoxin (Compound (1))

(1) Synthesis of 4-N-(4-chloro-3-methylaniline)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxin and 2 mol of 4-chloro-3-methylaniline, adding 0.36 g of $BaCO_3$, stirring for reaction at 25° C. for 24 hours; reaction liquid is rotary dried, then obtaining crude product of 4-N-(4-chloro-3-methylaniline)-4-deoxy-podophyllotoxin.

(2) Separation and purification of 4-N-(4-chloro-3-methylaniline)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(4-chloro-3-methylaniline)-4-deoxy-podophyllotoxin.

4-N-(4-chloro-3-methylaniline)-4-deoxy-podophyllotoxin: white powder: $C_{29}H_{28}ClNO_7$; 537, $^1$H NMR (300 MHz, $CDCl_3$): δ 2.297 (s, 3H, —$CH_3$), 2.977 (m, 1H, 2-H), 3.089 (d, J=13.5 Hz, 1H, 3-H), 3.737 (s, 6H, 3', 5'-$OCH_3$), 3.794 (s, 3H, 4'-$OCH_3$), 3.956 (t, J=9.3 Hz, 1H, 11-H), 4.359 (t, J=7.9 Hz, 1H, 11-H), 4.574 (d, J=12.6 Hz, 2H, 4-H, 1-H), 5.949 (t, J=2.5 Hz, 2H, $OCH_2O$), 6.303 (s, 3H, ArH), 6.412 (s, 1H, ArH), 6.510 (s, 1H, ArH), 6.731 (d, J=1.5 Hz, 1H, ArH), 7.122 (t, J=8.7 Hz, 1H, ArH) $^{13}$C NMR (75 MHz, $CDCl_3$): δ 20.512, 38.814, 41.937, 43.696, 52.826, 56.399, 60.901, 68.975, 101.711, 108.393, 109.237, 110.053, 110.996, 114.864, 123.558, 129.959, 130.550, 131.872, 135.206, 137.176, 146.165, 147.783, 148.430, 152.748, 174.849

Embodiment 2: synthesis and purification of 4-N-(4-chloro-3-methylaniline)-4-deoxy-4'-demethylepipodophyllotoxin (Compound (2))

(1) Synthesis of 4-N-(4-chloro-3-methylaniline)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 4-chloro-3-methylaniline, adding 0.36 g of $BaCO_3$, stirring for reaction at 25° C. for 24 hours; reaction liquid is rotary dried, then obtaining crude product of 4-N-(4-chloro-3-methylaniline)-4-deoxy-4'-demethylepipodophyllotoxin.

(2) Separation and purification of 4-N-(4-chloro-3-methylaniline)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=10:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(4-chloro-3-methylaniline)-4-deoxy-4'-demethylepipodophyllotoxin.

4-N-(4-chloro-3-methylaniline)-4-deoxy-4'-demethylepipodophyllotoxin: white powder: $C_{28}H_{26}ClNO_7$; 523; $^1$H NMR (300 MHz, $CDCl_3$): δ 2.303 (s, 3H, —$CH_3$), 2.965-3.012 (m, 1H, 2-H), 3.071 (dd, J=4.8 Hz, 1H, 3-H), 3.775 (s, 6H, 3', 5'-$OCH_3$), 3.950 (t, J=9.3 Hz, 1H, 11-H), 4.349 (t, J=7.8 Hz, 1H, 11-H), 4.556 (dd, J=4.8 Hz, 2H, 4-H, 1-H), 5.937 (d, J=6.6 Hz 2H, $OCH_2O$), 6.316 (s, 3H, ArH), 6.421 (s, 1H, ArH), 6.508 (s, 1H, ArH), 6.740 (s, 1H, ArH), 7.126 (d, J=8.1 Hz, 1H, ArH) $^{13}$C NMR (75 MHz, $CDCl_3$): δ 20.614, 38.855, 42.090, 43.604, 52.836, 56.695, 69.103, 101.785, 108.152, 109.369, 110.126, 111.076, 114.935, 123.484, 130.029, 130.682, 130.816, 132.122, 134.289, 137.243, 146.356, 146.682, 147.781, 148.463, 175.120

Embodiment 3: synthesis and purification of 4-N-(3-fluoro-4-methoxyaniline)-4-deoxy-podophyllotoxin (Compound (3))

(1) Synthesis of 4-N-(3-fluoro-4-methoxyaniline)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of 3-fluoro-4-methoxyaniline, adding 0.36 g of $BaCO_3$, stirring for reaction at 25° C. for 24 hours; reaction liquid is rotary dried, then obtaining crude product of 4-N-(3-fluoro-4-methoxyaniline)-4-deoxy-podophyllotoxin.

(2) Separation and purification of 4-N-(3-fluoro-4-methoxyaniline)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(3-fluoro-4-methoxyaniline)-4-deoxy-podophyllotoxin.

4-N-(3-fluoro-4-methoxyaniline)-4-deoxy-podophyllotoxin: white powder: $C_{29}H_{28}FNO_8$; 537; $^1$H NMR (300 MHz, $CDCl_3$): 2.997-3.009 (m, 1H, 2-H), 3.110 (dd, J=4.8 Hz, 1H, 3-H), 3.757 (s, 6H, 3', 5'-$OCH_3$), 3.808 (d, J=8.1 Hz, 6H, 4'-$OCH_3$, Ar—$OCH_3$) 3.995 (t, J=9.9 Hz, 1H, 11-H), 4.386 (t, J=7.5 Hz, 1H, 11-H), 4.579 (t, J=5.1 Hz, 2H, 4-H, 1-H), 5.952 (d, J=5.1 Hz 2H, $OCH_2O$), 6.235 (d, J=9.0 Hz, 1H, ArH), 6.315 (s, 2H, ArH), 6.380 (s, 1H, ArH), 6.520 (s, 1H, ArH), 6.755 (s, 1H, ArH), 6.853 (t, J=9.0 Hz, 1H, ArH) $^{13}$C NMR (75 MHz, $CDCl_3$): δ 38.890, 42.013, 43.814, 53.436, 56.503, 57.713, 61.005, 69.051, 101.576, 101.801, 107.456, 108.497, 109.285, 110.185, 116.375, 130.696, 131.962, 135.338, 142.738, 147.887, 148.534, 153.867, 175.009

Embodiment 4: synthesis and purification of 4-N-(3-fluoro-4-methoxyaniline)-4-deoxy-4'-demethyl-epipodophyllotoxin (Compound (4))

(1) Synthesis of 4-N-(3-fluoro-4-methoxyaniline)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 3-fluoro-4-methoxyaniline, adding 0.36 g of $BaCO_3$, stirring for reaction at 25° C. for 48 hours; reaction liquid is rotary dried, then obtaining crude product of 4-N-(3-fluoro-4-methoxyaniline)-4-deoxy-4'-demethylepipodophyllotoxin.

(2) Separation and purification of 4-N-(3-fluoro-4-methoxyaniline)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=20:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=10:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(3-fluoro-4-methoxyaniline)-4-deoxy-4'-demethylepipodophyllotoxin.

4-N-(3-fluoro-4-methoxyaniline)-4-deoxy-4'-demethylepipodophyllotoxin: white powder: $C_{28}H_{26}FNO_8$; 523, $^1H$ NMR (300 MHz, $CDCl_3$): 2.953-2.987 (m, 1H, 2-H), 3.079 (dd, J=4.8 Hz, 1H, 3-H), 3.773 (s, 6H, 3', 5'-$OCH_3$), 3.826 (s, 3H, Ar—$OCH_3$) 3.971 (t, J=7.8 Hz, 1H, 11-H), 4.354 (t, J=7.5 Hz, 1H, 11-H), 4.552 (s, 2H, 4-H, 1-H), 5.932 (d, J=7.8 Hz 2H, $OCH_2O$), 6.226 (d, J=9.0 Hz, 1H, ArH), 6.314 (s, 2H, ArH), 6.367 (s, 1H, ArH), 6.502 (s, 1H, ArH), 6.744 (s, 1H, ArH), 6.853 (t, J=9.0 Hz, 1H, ArH) $^{13}C$ NMR (75 MHz, $CDCl_3$): δ 38.810, 42.090, 43.619, 53.400, 56.695, 57.704, 69.073, 101.533, 107.425, 108.137, 109.280, 110.156, 116.286, 130.712, 130.816, 132.107, 134.289, 142.779, 146.682, 147.810, 148.478, 175.105

Embodiment 5: synthesis and purification of 4-N-(4,4'-diaminodiphenylmethane)-4-deoxy-podophyllotoxin (Compound (5))

(1) Synthesis of 4-N-(4,4'-diaminodiphenylmethane)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of 4,4'-diaminodiphenylmethane, adding 0.36 g of $BaCO_3$, stirring for reaction at 25° C. for 48 hours; reaction liquid is rotary dried, then obtaining crude product of 4-N-(4,4'-diaminodiphenylmethane)-4-deoxy-podophyllotoxin.

(2) Separation and purification of 4-N-(4,4'-diaminodiphenylmethane)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=15:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=10:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(4,4'-diaminodiphenylmethane)-4-deoxy-podophyllotoxin.

4-N-(4,4'-diaminodiphenylmethane)-4-deoxy-podophyllotoxin: white powder: $C_{35}H_{34}N_2O_7$; 594, $^1H$ NMR (300 MHz, $CDCl_3$): δ 3.266-3.331 (m, 2H, 2-H, 3-H), 3.651 (s, 6H, 3', 5'-$OCH_3$), 3.708 (s, 3H, 4'-$OCH_3$), 3.935 (t, J=9.3 Hz, 1H, 11-H), 4.411 (t, J=7.8 Hz, 1H, 11-H), 4.618 (d, J=1.8 Hz, 2H, 1-H, 4-H), 5.928 (s, 2H, $OCH_2O$), 6.268 (s, 4H, ArH), 6.414-6.497 (m, 6H, ArH), 6.556 (d, J=8.1 Hz, 4H, ArH), 6.714 (s, 2H, ArH), 6.806 (d, J=7.8 Hz, 2H, ArH), 6.868 (d, J=8.1 Hz, 2H, ArH) $^{13}C$ NMR (75 MHz, $CDCl_3$): δ 39.192, 41.414, 43.665, 51.206, 56.523, 60.631, 69.295, 101.821, 108.911, 109.811, 112.484, 114.763, 129.675, 129.815, 130.687, 132.432, 136.652, 147.147, 147.737, 152.661, 175.535

Embodiment 6: synthesis and purification of 4-N-(4,4'-diaminodiphenylmethane)-4-deoxy-4'-demethylepipodophyllotoxin (Compound (6))

(1) Synthesis of 4-N-(4,4'-diaminodiphenylmethane)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 4,4'-diaminodiphenylmethane, adding 0.36 g of $BaCO_3$, stirring for reaction at 25° C. for 24 hours; reaction liquid is rotary dried, then obtaining crude product of 4-N-(4,4'-diaminodiphenylmethane)-4-deoxy-4'-demethylepipodophyllotoxin.

(2) Separation and purification of 4-N-(4,4'-diaminodiphenylmethane)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(4,4'-diaminodiphenylmethane)-4-deoxy-4'-demethylepipodophyllotoxin.

4-N-(4,4'-diaminodiphenylmethane)-4-deoxy-4'-demethylepipodophyllotoxin: white powder: $C_{34}H_{32}N_2O_7$; 580, $^1$H NMR (300 MHz, $CDCl_3$): δ 2.988 (m, 1H, 2-H), 3.116 (dd, J=4.8 Hz, 1H, 3-H), 3.784 (s, 6H, 3', 5'-$OCH_3$), 4.000 (t, J=7.1 Hz, 1H, 11-H), 4.352 (t, J=7.8 Hz, 1H, 11-H), 4.591-4.624 (m, 2H, 1-H, 4-H), 5.943 (d, J=4.2 Hz, 2H, $OCH_2O$), 6.326 (s, 2H, ArH), 6.444-6.511 (m, 3H, ArH), 6.617 (d, J=8.1 Hz, 2H, ArH), 6.755 (s, 1H, ArH), 6.960-7.021 (m, 3H, ArH), 7.021 (s, 2H, ArH), 7.528 (d, J=3.6 Hz, 1H, ArH), 7.688 (d, J=5.4 Hz, 1H, ArH) $^{13}$C NMR (75 MHz, $CDCl_3$): δ 39.192, 41.414, 43.665, 51.281, 56.692, 69.244, 101.739, 109.214, 109.772, 112.477, 114.765, 129.631, 129.799, 130.133, 130.663, 131.054, 132.281, 135.377, 147.092, 147.706, 147.817, 175.571

Embodiment 7: synthesis and purification of 4-N-(o-aminoanisole)-4-deoxy-podophyllotoxin (Compound (7))

(1) Synthesis of 4-N-(o-aminoanisole)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of o-aminoanisole, adding 0.36 g of $BaCO_3$, stirring for reaction at 25° C. for 24 hours; reaction liquid is rotary dried, then obtaining crude product of 4-N-(o-aminoanisole)-4-deoxy-podophyllotoxin.

(2) Separation and purification of 4-N-(o-aminoanisole)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(o-aminoanisole)-4-deoxy-podophyllotoxin.

4-N-(o-aminoanisole)-4-deoxy-podophyllotoxin: white powder: $C_{29}H_{29}NO_8$; 519, $^1$H NMR (300 MHz, $CDCl_3$): δ 2.943-2.977 (m, 1H, 2-H), 3.142 (dd, J=4.8 Hz, 1H, 3-H), 3.700 (s, 6H, 3', 5'-$OCH_3$), 3.700 (s, 6H, Ar—$OCH_3$, 4'-$OCH_3$), 3.911 (t, J=9.9 Hz, 1H, 11-H), 4.321 (t, J=7.8 Hz, 1H, 11-H), 4.551 (d, J=4.5 Hz, 1H, 4-H), 4.606 (d, J=3.6 Hz, 1H, 1-H), 5.898 (s, 2H, $OCH_2O$), 6.273 (s, 2H, ArH), 6.421-6.469 (m, 2H, ArH), 6.663-6.760 (m, 3H, ArH), 6.825 (t, J=7.5 Hz, 1H, ArH) $^{13}$C NMR (75 MHz, $CDCl_3$): δ39.156, 42.140, 43.911, 52.488, 55.640, 56.547, 60.996, 69.252, 101.719, 108.665, 109.167, 109.627, 110.045, 117.841, 121.412, 131.118, 132.067, 135.525, 137.561, 146.571, 147.812, 148.426, 152.861, 175.105

Embodiment 8: synthesis and purification of 4-N-(o-aminoanisole)-4-deoxy-4'-demethylepipodophyllotoxin (Compound (8))

(1) Synthesis of 4-N-(o-aminoanisole)-4-deoxy-4'-demethylepipodophyllotoxin (Compound (8)): taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of o-aminoanisole, adding 0.36 g of $BaCO_3$, stirring for reaction at 25° C. for 24 hours; reaction liquid is rotary dried, then obtaining crude product of 4-N-(o-aminoanisole)-4-deoxy-4'-demethylepipodophyllotoxin.

(2) Separation and purification of 4-N-(o-aminoanisole)-4-deoxy-4'-demethylepipodophyllotoxin (Compound (8)):

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=8:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=4:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(o-aminoanisole)-4-deoxy-4'-demethylepipodophyllotoxin.

4-N-(o-aminoanisole)-4-deoxy-4'-demethylepipodophyllotoxin: white powder: $C_{28}H_{27}NO_8$; 505, $^1H$ NMR (300 MHz, $CDCl_3$): δ 2.985-3.019 (m, 1H, 2-H), 3.170 (dd, J=4.8 Hz, 1H, 3-H), 3.783 (s, 6H, 3', 5'-$OCH_3$), 3.811 (s, 3H, Ar—$OCH_3$), 3.944 (t, J=9.3 Hz, 1H, 11-H), 4.357 (t, J=7.8 Hz, 1H, 11-H), 4.596 (d, J=1.8 Hz, 1H, 4-H), 4.656 (d, J=3.3 Hz, 1H, 1-H), 5.949 (s, 2H, $OCH_2O$), 6.341 (s, 2H, ArH), 6.465 (d, J=7.8 Hz, 1H, ArH), 6.522 (s, 1H, ArH), 6.709-6.813 (m, 3H, ArH), 6.879 (t, J=7.5 Hz, 1H, ArH) $^{13}C$ NMR (75 MHz, $CDCl_3$): δ 39.058, 42.210, 43.688, 52.419, 55.626, 56.714, 69.252, 101.705, 108.190, 109.069, 109.585, 109.948, 110.031, 117.744, 121.384, 131.007, 131.090, 132.192, 134.256, 137.575, 146.501, 146.668, 147.742, 148.384, 175.231

Embodiment 9: synthesis and purification of 4-N-(4-chloro-2-aminoanisole)-4-deoxy-podophyllotoxin (Compound (9))

(1) Synthesis of 4-N-(4-chloro-2-aminoanisole)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of 4-chloro-2-aminoanisole, adding 0.36 g of $BaCO_3$, stirring for reaction at 25° C. for 24 hours; reaction liquid is rotary dried, then obtaining crude product of 4-N-(4-chloro-2-aminoanisole)-4-deoxy-podophyllotoxin.

(2) Separation and purification of 4-N-(4-chloro-2-aminoanisole)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=6:1 as developing solvent, fractions with Rf value of 0.5 are combined; sample of white powder from vacuum drying is 4-N-(4-chloro-2-aminoanisole)-4-deoxy-podophyllotoxin.

4-N-(4-chloro-2-aminoanisole)-4-deoxy-podophyllotoxin: white powder: $C_{29}H_{28}ClNO_8$; 553, $^1H$ NMR (300 MHz, $CDCl_3$): δ3.015-3.050 (m, 1H), 3.133 (dd, J=4.8 Hz, 1H), 3.752 (s, 6H), 3.783 (s, 3H), 3.802 (s, 3H), 3.905 (t, J=9.6 Hz, 1H), 4.399 (t, J=7.9 Hz, 1H), 4.601 (d, J=5.1 Hz, 2H), 5.954 (d, J=2.4 Hz, 2H), 6.318 (s, 2H), 6.432 (s, 1H), 6.521 (s, 1H), 6.665 (s, 2H), 6.728 (s, 1H) $^{13}C$ NMR (75 MHz, $CDCl_3$): δ38.935, 42.114, 43.844, 52.238, 55.850, 56.461, 61.014, 69.001, 101.815, 108.352, 108.962, 109.548, 110.082, 110.540, 116.848, 126.463, 130.482, 132.085, 135.340, 137.325, 138.495, 145.057, 147.855, 148.542, 152.816, 174.971

Embodiment 10: synthesis and purification of 4-N-(4-chloro-2-aminoanisole)-4-deoxy-4'-demethylepipodophyllotoxin (Compound (10))

(1) Synthesis of 4-N-(4-chloro-2-aminoanisole)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 4-chloro-2-aminoanisole, adding 0.36 g of $BaCO_3$, stirring for reaction at 25° C. for 24 hours; reaction liquid is rotary dried, then obtaining crude product of 4-N-(4-chloro-2-aminoanisole)-4-deoxy-4'-demethylepipodophyllotoxin.

(2) Separation and purification of 4-N-(4-chloro-2-aminoanisole)-4-deoxy-4'-demethylepipodophyllotoxin (Compound (10)):

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=7:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(4-chloro-2-aminoanisole)-4-deoxy-4'-demethylepipodophyllotoxin.

4-N-(4-chloro-2-aminoanisole)-4-deoxy-4'-demethylepipodophyllotoxin: white powder: $C_{28}H_{26}ClNO_8$; 539, $^1H$ NMR (300 MHz, $CDCl_3$): δ3.039 (m, 1H), 3.114 (dd, J=4.8 Hz, 1H), 3.784 (s, 9H), 3.898 (t, J=9.3 Hz, 1H), 4.376 (t, J=7.8 Hz, 1H), 4.594 (d, J=5.1 Hz, 2H), 5.954 (d, J=3.0 Hz, 2H), 6.333 (s, 2H), 6.436 (s, 1H), 6.524 (s, 1H), 6.672 (s, 2H), 6.728 (s, 1H) $^{13}C$ NMR (75 MHz, $CDCl_3$): δ38.863, 42.210, 43.674, 52.251, 55.863, 56.700, 69.001, 101.789, 108.121, 108.985, 109.501, 110.101, 110.547, 126.488, 130.505, 130.784, 132.276, 134.284, 138.524, 145.065, 146.682, 147.798, 148.523, 175.008

Embodiment 11: synthesis and purification of 4-N-(o-aminobenzonitrile)-4-deoxy-podophyllotoxin (Compound (11))

(1) Synthesis of 4-N-(o-aminobenzonitrile)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxin and 2 mol of o-aminobenzonitrile, adding 0.36 g of $BaCO_3$, stirring for reaction at 25° C. for 24 hours; reaction liquid is rotary dried, then obtaining crude product of 4-N-(o-aminobenzonitrile)-4-deoxy-podophyllotoxin.

(2) Separation and purification of 4-N-(o-aminobenzonitrile)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=8:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(o-aminobenzonitrile)-4-deoxy-podophyllotoxin.

4-N-(o-aminobenzonitrile)-4-deoxy-podophyllotoxin: white powder: $C_{29}H_{26}N_2O_7$; 514, $^1H$ NMR (300 MHz, $CDCl_3$): δ3.025-3.084 (m, 1H), 3.135 (dd, J=4.8 Hz, 1H), 3.736 (s, 6H), 3.787 (s, 3H), 3.833 (t, J=9.9 Hz, 1H), 4.351 (t, J=7.8 Hz, 1H), 4.629 (d, J=4.8 Hz, 1H), 4.726 (s, 2H), 5.817 (s, 1H), 5.945 (s, 1H), 6.310 (s, 2H), 6.509 (s, 1H) 6.573 (d, J=8.7 Hz, 1H), 6.740 (s, 1H), 6.778 (d, J=7.8 Hz, 1H), 7.432 (t, J=7.5 Hz, 2H) $^{13}C$ NMR (75 MHz, $CDCl_3$): δ 38.063, 41.849, 43.734, 52.320, 56.483, 61.011, 68.577, 96.404, 101.927, 108.393, 109.309, 110.147, 110.252, 117.634, 118.210, 129.100, 132.388, 133.733, 134.859, 135.147, 137.372, 147.974, 148.864, 149.387, 152.843, 174.466

Embodiment 12: synthesis and purification of 4-N-(o-aminobenzonitrile)-4-deoxy-4'-demethylepipodophyllotoxin (Compound (12))

(1) Synthesis of 4-N-(o-aminobenzonitrile)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of o-aminobenzonitrile, adding 0.36 g of $BaCO_3$, stirring for reaction at 25° C. for 24 hours; reaction liquid is rotary dried, then obtaining crude product of 4-N-(o-aminobenzonitrile)-4-deoxy-4'-demethylepipodophyllotoxin.

(2) Separation and purification of 4-N-(o-aminobenzonitrile)-4-deoxy-4'-demethylepipodophyllotoxin (Compound (12)):

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(o-aminobenzonitrile)-4-deoxy-4'-demethylepipodophyllotoxin.

4-N-(o-aminobenzonitrile)-4-deoxy-4'-demethylepipodophyllotoxin: white powder; $C_{28}H_{24}N_2O_7$; 500, $^1H$ NMR (300 MHz, $CDCl_3$): δ3.065 (m, 1H), 3.123 (dd, J=4.5 Hz, 1H), 3.789 (s, 6H), 3.847 (t, J=9.0 Hz, 1H), 4.351 (t, J=7.5 Hz, 1H), 4.635 (d, J=4.2 Hz, 1H), 4.732 (s, 1H), 4.800 (s, 1H), 5.901 (s, 1H), 5.981 (s, 1H), 6.333 (s, 2H), 6.533 (s, 1H), 6.597 (d, J=8.7 Hz, 1H), 6.740 (s, 1H), 6.801 (t, J=7.5 Hz, 1H), 7.443 (d, J=6.9 Hz, 2H) $^{13}C$ NMR (75 MHz, $CDCl_3$): δ 38.556, 41.973, 43.577, 52.363, 56.756, 68.555, 96.573, 101.900, 108.274, 109.222, 110.240, 110.320, 118.218, 129.110, 130.574, 132.555, 133.712, 134.437, 134.832, 146.724, 148.007, 148.914, 149.388, 174.408

Embodiment 13: synthesis and purification of 4-N-(2,6-dichloro-4-aminophenol)-4-deoxy-podophyllotoxin (Compound (13))

(1) Synthesis of 4-N-(2,6-dichloro-4-aminophenol)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand 2 mol of 2,6-dichloro-4-aminophenol, adding 0.36 g of $BaCO_3$, stirring for reaction at 25° C. for 12 hours; reaction liquid is rotary dried, then obtaining crude product of 4-N-(2,6-dichloro-4-aminophenol)-4-deoxy-podophyllotoxin.

(2) Separation and purification of 4-N-(2,6-dichloro-4-aminophenol)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=30:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=15:1 as developing solvent, fractions with Rf value of 0.5 are combined; sample of white powder from vacuum drying is 4-N-(2,6-dichloro-4-aminophenol)-4-deoxy-podophyllotoxin.

4-N-(2,6-dichloro-4-aminophenol)-4-deoxy-podophyllotoxin: white powder: $C_{28}H_{25}Cl_2NO_8$; 573, $^1H$ NMR (300 MHz, $CDCl_3$): δ2.862-3.129 (m, 2H), 3.734 (s, 6H), 3.781 (s, 3H), 3.958 (t, J=9.3 Hz, 1H), 4.391 (t, J=7.2 Hz, 1H), 4.537 (d, J=13.5 Hz, 1H), 5.939 (d, J=7.2, 2H), 6.275 (s, 2H), 6.487 (s, 3H), 6.699 (s, 1H) $^{13}C$ NMR (75 MHz, $CDCl_3$): δ 38.688, 41.979, 43.723, 53.471, 56.456, 61.016, 68.840, 101.879, 108.308, 109.187, 110.247, 112.492, 122.241, 130.107, 132.003, 135.169, 137.345, 140.734, 141.654, 147.916, 148.627, 152.825, 174.847

Embodiment 14: synthesis and purification of 4-N-(2,6-dichloro-4-aminophenol)-4-deoxy-4'-demethylepipodophyllotoxin (Compound (14))

(1) Synthesis of 4-N-(2,6-dichloro-4-aminophenol)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 2,6-dichloro-4-aminophenol, adding 0.36 g of $BaCO_3$, stirring for reaction at 25° C. for 12 hours; reaction liquid is rotary dried, then obtaining crude product of 4-N-(2,6-dichloro-4-aminophenol)-4-deoxy-4'-demethyl-epipodophyllotoxin.

(2) Separation and purification of 4-N-(2,6-dichloro-4-aminophenol)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2,6-dichloro-4-aminophenol)-4-deoxy-4'-demethylepipodophyllotoxin.

4-N-(2,6-dichloro-4-aminophenol)-4-deoxy-4'-demethylepipodophyllotoxin: white powder: $C_{27}H_{23}Cl_2NO_8$; 560, $^1$H NMR (300 MHz, $CDCl_3$): δ2.999-3.094 (m, 2H), 3.755 (s, 6H), 3.932 (t, J=9.0 Hz, 1H), 4.365 (t, J=7.2 Hz, 1H), 4.537 (s, 1H), 5.917 (d, J=11.1, 2H), 6.292 (s, 2H), 6.497 (s, 3H), 6.709 (s, 1H) $^{13}$C NMR (75 MHz, $CDCl_3$): δ 38.661, 42.062, 43.556, 53.345, 56.704, 68.906, 101.851, 108.062, 109.213, 110.214, 112.408, 122.293, 130.217, 130.669, 132.164, 134.248, 140.613, 141.816, 146.669, 147.807, 148.547, 175.063

Embodiment 15: synthesis and purification of 4-N—(N,N-dimethylamino metanil)-4-deoxy-podophyllotoxin (Compound (15))

(1) Synthesis of 4-N—(N,N-dimethylamino metanil)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of N,N-dimethylamino metanil, adding 0.36 g of $BaCO_3$, stirring for reaction at 25° C. for 24 hours; reaction liquid is rotary dried, then obtaining crude product of 4-N—(N,N-dimethylamino metanil)-4-deoxy-podophyllotoxin.

(2) Separation and purification of 4-N—(N,N-dimethylamino metanil)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=4:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=2:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N—(N,N-dimethylamino metanil)-4-deoxy-podophyllotoxin.

4-N—(N,N-dimethylamino metanil)-4-deoxy-podophyllotoxin: white powder: $C_{30}H_{32}N_2O_7$; 532, $^1$H NMR (300 MHz, $CDCl_3$): δ2.936 (s, 6H), 2.996 (d, J=2.7 Hz, 1H), 3.143 (dd, J=4.5 Hz, 2H), 3.757 (s, 6H), 3.804 (s, 3H), 4.049 (t, J=9.6 Hz, 1H), 4.399 (t, J=8.1 Hz, 1H), 4.586 (d, J=4.5 Hz, 1H), 4.688 (s, 1H), 5.947 (d, J=4.5, 4H), 6.231 (d, J=8.1 Hz, 1H), 6320 (s, 2H), 6.513 (s, 1H), 6.800 (s, 1H), 7.092 (t, J=8.1 Hz, 1H) $^{13}$C NMR (75 MHz, $CDCl_3$): δ 39.050, 41.101, 42.049, 43.820, 52.676, 56.497, 61.016, 69.468, 101.768, 104.055, 108.420, 109.564, 110.080, 130.455, 131.097, 131.920, 135.518, 137.317, 147.805, 148.390, 148.697, 152.797, 175.265

Embodiment 16: synthesis and purification of 4-N—(N,N-dimethylamino metanil)-4-deoxy-4'-demethylepipodophyllotoxin (Compound (16))

(1) Synthesis of 4-N—(N,N-dimethylamino metanil)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of N,N-dimethylamino metanil, adding 0.36 g of $BaCO_3$, stirring for reaction at 25° C. for 24 hours; reaction liquid is rotary dried, then obtaining crude product of 4-N—(N,N-dimethylamino metanil)-4-deoxy-4'-demethylepipodophyllotoxin.

(2) Separation and purification of 4-N—(N,N-dimethylamino metanil)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=12:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=6:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N—(N,N-dimethylamino metanil)-4-deoxy-4'-demethylepipodophyllotoxin.

4-N—(N,N-dimethylamino metanil)-4-deoxy-4'-demethylepipodophyllotoxin: white powder: $C_{29}H_{30}N_2O_7$; 518, $^1H$ NMR (300 MHz, CDCl$_3$): δ2.928 (s, 6H), 2.978 (d, J=3.3 Hz, 1H), 3.119 (dd, J=4.5 Hz, 2H), 3.777 (s, 6H), 4.032 (t, J=9.6 Hz, 1H), 4.372 (t, J=7.8 Hz, 1H), 4.564 (d, J=4.8 Hz, 1H), 4.672 (d, J=2.7 Hz, 1H), 5.933 (d, J=5.7, 4H), 6.222 (d, J=8.1 Hz, 1H), 6326 (s, 2H), 6.501 (s, 1H), 6.793 (s, 1H), 7.084 (t, J=8.1 Hz, 1H) $^{13}C$ NMR (75 MHz, CDCl$_3$): δ 38.855, 40.905, 41.979, 43.499, 52.495, 56.567, 69.356, 101.600, 103.846, 107.974, 109.410, 109.926, 130.274, 130.846, 130.999, 131.948, 134.067, 146.508, 147.609, 148.209, 148.586, 151.654, 175.237

Embodiment 17: synthesis and purification of 4-N-(2-ethyl-5-nitroaniline)-4-deoxy-podophyllotoxin (Compound (17))

(1) Synthesis of 4-N-(2-ethyl-5-nitroaniline)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of 2-ethyl-5-nitroaniline, adding 0.36 g of BaCO$_3$, stirring for reaction at 25° C. for 24 hours; reaction liquid is rotary dried, then obtaining crude product of 4-N-(2-ethyl-5-nitroaniline)-4-deoxy-podophyllotoxin.

(2) Separation and purification of 4-N-(2-ethyl-5-nitroaniline)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column; glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2-ethyl-5-nitroaniline)-4-deoxy-podophyllotoxin.

4-N-(2-ethyl-5-nitroaniline)-4-deoxy-podophyllotoxin: white powder: $C_{30}H_{30}N_2O_9$; 562, $^1H$ NMR (300 MHz, CDCl$_3$): δ 1.237 (t, J=7.2 Hz, 3H), 2.449-2.522 (m, 2H), 3.116 (s, 2H), 3.759 (s, 6H), 3.799 (s, 3H) 4.002 (d, J=5.1 Hz, 1H), 4.452 (t, J=3.6 Hz, 1H), 4.618 (s, 1H), 4.826 (s, 1H), 5.967 (d, J=1.2 Hz, 2H), 6.309 (s, 2H), 6.546 (s, 1H), 6.706 (s, 1H), 7.211 (d, J=8.4 Hz, 1H), 7.317 (t, J=1.5 Hz, 1H), 7.609 (d, J=8.4 Hz, 1H) $^{13}C$ NMR (75 MHz, CDCl$_3$): δ 12.543, 24.311, 38.656, 42.178, 43.810, 52.658, 56.466, 61.018, 68.836, 101.936, 103.282, 108.321, 109.037, 110.354, 113.561, 128.880, 129.882, 132.402, 134.850, 137.470, 145.487, 147.663, 148.121, 152.903, 174.607

Embodiment 18: synthesis and purification of 4-N-(2-ethyl-5-nitroaniline)-4-deoxy-4'-demethylepipodophyllotoxin (Compound (18))

(1) Synthesis of 4-N-(2-ethyl-5-nitroaniline)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 2-ethyl-5-nitroaniline, adding 0.36 g of BaCO$_3$, stirring for reaction at 25° C. for 24 hours; reaction liquid is rotary dried, then obtaining crude product of 4-N-(2-ethyl-5-nitroaniline)-4-deoxy-4'-demethylepipodophyllotoxin.

(2) Separation and purification of 4-N-(2-ethyl-5-nitroaniline)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2-ethyl-5-nitroaniline)-4-deoxy-4'-demethylepipodophyllotoxin.

4-N-(2-ethyl-5-nitroaniline)-4-deoxy-4'-demethylepipodophyllotoxin: white powder: $C_{28}H_{26}N_2O_7$; 502; $^1$H NMR (300 MHz, $CDC_{13}$): δ 1.248 (s, 3H), 2.549 (d, J=7.2 Hz, 2H), 3.129 (s, 2H), 3.809 (s, 6H), 4.004 (s, 1H), 4.453 (s, 1H), 4.631 (s, 1H), 4.849 (s, 1H), 5.986 (d, J=2.4 Hz, 2H), 6.339 (s, 2H), 6.563 (s, 1H), 6.724 (s, 1H), 7.231 (d, J=9.3 Hz, 1H), 7.342 (s, 1H), 7.634 (d, J=9.6 Hz, 1H) $^{13}$C NMR (75 MHz, $CDCl_3$): δ 12.571, 24.340, 38.599, 42.293, 43.667, 52.672, 56.710, 68.879, 101.950, 103.282, 108.063, 109.037, 110.354, 113.518, 128.894, 129.911, 130.440, 132.662, 134.377, 134.778, 145.544, 146.733, 147.678, 148.079, 148.809, 174.779

Embodiment 19: synthesis and purification of 4-N-(2 2'-diaminodiphenylsulfide)-4-deoxy-podophyllotoxin (Compound (19))

(1) Synthesis of 4-N-(2 2'-diaminodiphenylsulfide)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of 2 2'-diaminodiphenylsulfide, adding 0.36 g of $BaCO_3$, stirring for reaction at 25° C. for 24 hours; reaction liquid is rotary dried, then obtaining crude product of 4-N-(2 2'-diaminodiphenylsulfide)-4-deoxy-podophyllotoxin.

(2) Separation and purification of 4-N-(2 2'-diaminodiphenylsulfide)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform:acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2 2'-diaminodiphenylsulfide)-4-deoxy-podophyllotoxin.

4-N-(2 2'-diaminodiphenylsulfide)-4-deoxy-podophyllotoxin: white powder: $C_{34}H_{32}N_2O_{7S}$; 612; $^1$H NMR (300 MHz, $CDCl_3$): δ2.586 (dd, J=5.1 Hz, 1H, 3-H), 2.8077-2.866 (m, 1H, 2-H), 3.383 (t, J=9.6 Hz, 1H, 11-H), 3.735 (s, 6H, 3', 5'-$OCH_3$), 3.789 (s, 3H, 4'-$OCH_3$), 4.144 (t, J=7.9 Hz, 1H, 11-H), 4.482 (d, J=5.1 Hz, 1H, 1-H), 4.721 (s, 1H, 4-H), 5.946 (d, J=5.1 Hz, 2H, $OCH_2O$), 6.279 (s, 2H, ArH), 6.424 (s, 1H, ArH), 6.526 (d, J=8.1 Hz, 1H, ArH), 6.625 (s, 2H, ArH), 6.714 (t, J=7.5 Hz, 1H, ArH), 7.037 (d, J=7.8 Hz, 2H, ArH), 7.228 (t, J=9.0 Hz, 1H, ArH), 7.513 (d, J=7.2 Hz, 1H, ArH) $^{13}$C NMR (75 MHz, $CDCl_3$): δ 38.6648, 41.6062, 43.6227, 51.0699, 56.3359, 60.8768, 66.6776, 101.5862, 108.2271, 109.1747, 109.4324, 109.7205, 115.4507, 116.7025, 117.0653, 119.5453, 129.6658, 130.3405, 131.7809, 133.1682, 135.5941, 137.1178, 146.6470, 147.4885, 148.2067, 152.6208, 174.7949

Embodiment 20: synthesis and purification of 4-N-(2 2'-diaminodiphenylsulfide)-4-deoxy-4'-demethylepipodophyllotoxin (Compound (20))

(1) Synthesis of 4-N-(2 2'-diaminodiphenylsulfide)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 2 2'-diaminodiphenylsulfide, adding 0.36 g of $BaCO_3$, stirring for reaction at 25° C. for 24 hours; reaction liquid is rotary dried, then obtaining crude product of 4-N-(2 2'-diaminodiphenylsulfide)-4-deoxy-4'-demethylepipodophyllotoxin.

(2) Separation and purification of 4-N-(2 2'-diaminodiphenylsulfide)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform: acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2 2'-diaminodiphenylsulfide)-4-deoxy-4'-demethylepipodophyllotoxin.

4-N-(2 2'-diaminodiphenylsulfide)-4-deoxy-4'-demethylepipodophyllotoxin: white powder: $C_{33}H_{30}N_2O_7S$; 598, $^1$H NMR (300 MHz, $CDCl_3$): δ 2.841 (s, 1H, 2-H), 3.402 (t, J=9.6 Hz, 1H, 3-H), 3.771 (s, 6H, 3', 5'-$OCH_3$), 3.944 (t, J=9.3 Hz, 1H, 11-H), 4.357 (t, J=7.8 Hz, 1H, 11-H), 4.387 (d, J=1.8 Hz, 1H, 4-H), 4.514 (d, J=3.3 Hz, 1H, 1-H), 5.926 (s, 2H, $OCH_2O$), 6.291 (s, 2H, ArH), 6.465 (d, J=7.8 Hz, 1H, ArH), 6.5955 (s, 1H, ArH), 6.709-6.813 (m, 3H, ArH), 6.874 (t, J=7.5 Hz, 1H, ArH) $^{13}$C NMR (75 MHz, $CDCl_3$): δ 38.725, 41.862, 43.592, 53.691, 56.714, 68.815, 101.691, 108.134, 109.344, 109.513, 109.893, 115.675, 117.222, 117.827, 119.768, 129.799, 130.460, 130.980, 132.134, 133.302, 134.258, 135.721, 146.651, 146.849, 147.608, 148.368, 175.012

Embodiment 21: synthesis and purification of 4-N-(2-aminobenzotrifluoride)-4-deoxy-podophyllotoxin (Compound (21))

(1) Synthesis of 4-N-(2-aminobenzotrifluoride)-4-deoxy-podophyllotoxin: taking 1 mol of activated product of position 4 of C-ring of podophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of podophyllotoxinand and 2 mol of 2 2'-diaminodiphenylsulfide, adding 0.36 g of $BaCO_3$, stirring for reaction at 25° C. for 24 hours; reaction liquid is rotary dried, then obtaining crude product of 4-N-(2-aminobenzotrifluoride)-4-deoxy-podophyllotoxin.

(2) Separation and purification of 4-N-(2-aminobenzotrifluoride)-4-deoxy-podophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform: acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2-aminobenzotrifluoride)-4-deoxy-podophyllotoxin.

4-N-(2-aminobenzotrifluoride)-4-deoxy-podophyllotoxin: white powder: $C_{29}H_{26}F_3NO_7$; 557, $^1$H NMR (300 MHz, $CDCl_3$): δ 3.112 (s, 2H, 2-H, 3-H), 3.794 (s, 6H, 3', 5'-$OCH_3$), 3.846 (s, 3H, 4'-$OCH_3$), 3.935 (t, J=9.3 Hz, 1H, 11-H), 4.411 (t, J=7.8 Hz, 1H, 11-H), 4.668 (d, J=1.8 Hz, 1H, 4-H), 4.834 (d, J=3.3 Hz, 1H, 1-H), 6.009 (s, 2H, $OCH_2O$), 6.363 (s, 2H, ArH), 6.576 (s, 1H, ArH), 6.672 (d, J=8.1 Hz, 1H, ArH), 6.786 (s, 1H, ArH), 6.864 (t, J=7.5 Hz, 1H, ArH), 7.452 (t, J=7.2 Hz, 1H, ArH), 7.521 (d, J=7.5 Hz, 1H, ArH) $^{13}$C NMR (75 MHz, $CDCl_3$): δ 38.806, 42.122, 43.800, 52.466, 56.545, 61.019, 68.925, 101.899, 108.567, 109.271, 110.256, 111.353, 117.655, 127.488, 129.767, 132.229, 133.650, 135.212, 144.961, 148.098, 148.787, 152.909, 174.643

Embodiment 22: synthesis and purification of 4-N-(2-aminobenzotrifluoride)-4-deoxy-4'-demethylepipodophyllotoxin (Compound (20))

(1) Synthesis of 4-N-(2-aminobenzotrifluoride)-4-deoxy-4'-demethylepipodophyllotoxin: taking 1 mol of activated product of position 4 of C-ring of 4'-demethylepipodophyllotoxin (prepared in preparatory test example 1), which is then dried in vacuo at 45° C. for 2 hours; under protection of nitrogen, dried dichloromethane were added into a 4-necked flask, then adding dried activated product of position 4 of C-ring of 4'-demethylepipodophyllotoxin and 2 mol of 2-aminobenzotrifluoride, adding 0.36 g of $BaCO_3$, stirring for reaction at 25° C. for 24 hours; reaction liquid is rotary dried, then obtaining crude product of 4-N-(2-aminobenzotrifluoride)-4-deoxy-4'-demethylepipodophyllotoxin.

(2) Separation and purification of 4-N-(2-aminobenzotrifluoride)-4-deoxy-4'-demethylepipodophyllotoxin:

Separation and Purification Using Silica Gel Column Chromatography and Gel Column Chromatography:

(A) using normal phase silica gel column (normal phase silica gel: China Qingdao Haiyang Chemical Co., Ltd, HG/T2354-92; separation system: Swiss Buchi isocratic fast chromatography system; chromatographic column: Swiss Buchi glass column C-690 with length of 460 mm and inner diameter of 15 mm) or a similar polar column separation; taking system of chloroform:acetone=10:1 as eluent, with sample volume of 2 ml, constant flow rate of 1.0 ml/min; each of 2 ml of eluent as a fraction were collected. Using normal phase silica gel thin layer (efficient silica gel thin layer by Merck, Germany) or thin layer with similar polarity, each of fractions are viewed; taking system of chloroform: acetone=5:1 as a developing agent, fractions with Rf value of 0.5 are merged; the sample after merged is subjected to vacuum drying, stored at 4° C. in the refrigerator under dark conditions, as samples to be purified.

(B) separating by gel column chromatography (gel: Sephadex LH-20; Separation column: glass column with length 480 mm and inner diameter of 30 mm); loading processed gel Sephadex LH-20 into column by wet method to be balanced with methanol. The sample to be purified is dissolved in 6 ml of methanol, adsorbed at flow rate of 0.6 ml/min of sample and then eluted at flow rate of 0.6 ml/min with 600 ml of methanol, eluate was collected to a bottle every 10 ml, each fraction is checked with normal phase silica gel thin layer (effective silica gel thin layer by Merck, Germany) or thin layer with similar polar; adopting system with chloroform:acetone=5:1 as developing solvent, fractions with Rf value of 0.5 are combined; sample of white powder from vacuum drying is 4-N-(2-aminobenzotrifluoride)-4-deoxy-4'-demethylepipodophyllotoxin.

4-N-(2-aminobenzotrifluoride)-4-deoxy-4'-demethylepipodophyllotoxin: white powder: $C_{28}H_{24}F_3NO_7$; 543, $^1H$ NMR (300 MHz, $CDCl_3$): δ 3.088 (s, 2H, 2-H, 3-H), 3.810 (s, 6H, 3', 5'-$OCH_3$), 3.916 (t, J=9.3 Hz, 1H, 11-H), 4.411 (t, J=6.3 Hz, 1H, 11-H), 4.638 (d, J=3.6 Hz, 1H, 4-H), 4.821 (s, 1H, 1-H), 5.995 (s, 2H, $OCH_2O$), 6.369 (s, 2H, ArH), 6.562 (s, 1H, ArH), 6.662 (d, J=1.0 Hz, 1H, ArH), 6.771 (s, 1H, ArH), 6.850 (t, J=7.5 Hz, 1H, ArH), 7.441 (t, J=7.2 Hz, 1H, ArH), 7.509 (d, J=7.5 Hz, 1H, ArH) $^{13}C$ NMR (75 MHz, $CDCl_3$): δ 38.795, 42.196, 43.631, 52.480, 56.770, 68.925, 101.871, 108.230, 109.229, 110.256, 111.367, 117.613, 127.474, 129.767, 132.398, 133.650, 134.410, 144.975, 146.733, 148.041, 148.776, 152.909, 174.714

Experiment 1: Test of Compounds of Embodiment of the Present Invention on Inhibiting Tumor Cell Activity 1) Test Materials 1, compounds for the test: the compounds prepared in embodiments 1 to 22, noted with compounds (1) to (22);

2, compounds for comparison: podophyllotoxin and 4'-demethylepipodophyllotoxins;

3, cell lines: Hela, BGC823, A549 cell line and normal human hepatocytes which are available from Wu Han boster Co., Ltd.;

2) Test Method

Hela, BGC823, A549 cell line and normal human hepatocytes in logarithmic growth phase are subjected to 1000 rpm centrifugation for 5 min, supernatant is then discarded, moderate medium is suspended, the cell concentration is adjusted to $3.5 \times 10^4$/well, the cells were seeded in 96-wells culture plate, and following experimental groups are set:

a negative control group; 22 test groups with same concentration (ie: groups of Compound (1) to Compound (22)); 2 control groups: groups of podophyllotoxin, 4'-demethylepipodophyllotoxin and etoposide.

Taking RPMI1640 containing 10% of calf serum as nutrient solution, 0.10 mL of cells per well is incubated under conditions of 37 V, 5% CO2 and saturated humidity for 24 h to nearly be covered, then the nutrient solution is discarded. For the 22 test groups, 0.10 M of nutrient solution of RPMI1640 with 10% calf serum containing same amount of the compound (1) to compound (22) is added respectively; for groups of podophyllotoxin, 4'-demethylepipodophyllotoxin and etoposide, 0.10 M of nutrient solution of RPMI1640 with 10% calf serum is added containing podophyllotoxin, 4'-demethylepipodophyllotoxin and etoposide, respectively; amount of podophyllotoxin, 4'-demethylepipodophyllotoxin or etoposide is same as the amount of the compounds (1) to (22); for the negative control group, DMSO with a final concentration of 0.5% is added; for each group, three complex wells are set, cultivation is continued for 48 h, 10 μl of MTT with 5 mg/ml is added to each well, then put at 37° C. for 4 h. 100 μl of DMSO is added to each well, then vibrated at 37° C. by shaker table for 30 min, then measuring absorbance (OD) at 492 nm, calculating MTT ratio=OD value of drug group/OD value of the negative control group.

3) Test Results

Test results are shown in Table 1. From Table 1, antitumor activity of the compounds of aniline-substituted podophyllotoxin-type derivatives of embodiments of the invention to the Hela, BGC823, A549 cell lines is much better than those of podophyllotoxin, and 4'-demethylepipodophyllotoxin.

TABLE 1

$IC_{50}$ values of aniline-substituted podophyllotoxin-type derivatives to in vitro tumor cell lines and normal cell lines

| Compounds | Cytotoxic activity ($IC_{50}$, μM)[a] | | |
|---|---|---|---|
|  | Hela[b] | BGC823[b] | A549[b] |
| 1 | 1.26 ± 0.37 | 0.62 ± 0.13 | 1.75 ± 0.83 |
| 2 | 2.01 ± 1.21 | 1.77 ± 0.37 | 5.21 ± 0.41 |
| 3 | 2.57 ± 0.87 | 3.16 ± 1.11 | 1.97 ± 0.32 |
| 4 | 1.97 ± 0.16 | 0.40 ± 0.17 | 3.04 ± 0.23 |
| 5 | 7.07 ± 1.63 | 17.18 ± 0.34 | 2.32 ± 0.06 |
| 6 | 0.56 ± 0.17 | 3.52 ± 0.43 | 2.20 ± 0.25 |
| 7 | 13.37 ± 3.31 | 6.26 ± 0.36 | 3.41 ± 0.10 |
| 8 | 1.72 ± 0.30 | 5.63 ± 1.20 | 15.27 ± 0.45 |
| 9 | 8.07 ± 1.81 | 1.24 ± 0.06 | 1.71 ± 0.26 |
| 10 | 1.35 ± 0.18 | 1.61 ± 0.37 | 3.72 ± 0.41 |
| 11 | 16.91 ± 1.48 | >100 | 1.02 ± 0.07 |
| 12 | 1.92 ± 1.21 | 7.91 ± 0.59 | 11.64 ± 1.63 |
| 13 | 17.57 ± 2.39 | 1.58 ± 0.16 | 9.66 ± 0.35 |
| 14 | 14.67 ± 0.42 | 13.82 ± 1.42 | 9.41 ± 0.59 |
| 15 | 1.33 ± 0.20 | 2.59 ± 0.21 | >100 |
| 16 | 1.06 ± 0.57 | 1.52 ± 0.39 | 2.08 ± 0.26 |
| 17 | 6.01 ± 0.71 | 4.24 ± 0.79 | 1.4 ± 0.28 |
| 18 | 7.89 ± 0.31 | 27.12 ± 0.24 | 4.28 ± 0.48 |
| 19 | 2.14 ± 0.21 | 6.46 ± 0.33 | 23.24 ± 0.72 |
| 20 | 16.31 ± 0.39 | 2.17 ± 0.23 | 1.42 ± 0.12 |
| 21 | 2.45 ± 3.04 | 23.24 ± 0.76 | 2.11 ± 0.05 |
| 22 | 5.89 ± 0.48 | 6.01 ± 0.12 | 9.72 ± 0.98 |
| podophyllotoxin | 55 ± 0.24 | 75 ± 0.73 | 67 ± 0.24 |
| 4'-demethylepipodophyllotoxin | 49 ± 0.38 | 63 ± 0.49 | 52 ± 0.85 |
| VP-16 | 13.15 ± 1.65 | 22.32 ± 2.97 | 31.05 ± 1.72 |

The invention claimed is:

1. An analine-substituted podophyllotoxin-type derivative with anti-tumor activity or a salt thereof, with structural formula (V):

formula (V)

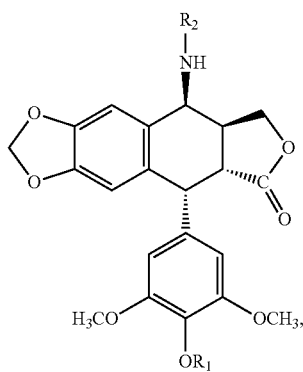

wherein, $R_1$ is hydrogen or methyl; and
$R_2$ is selected from

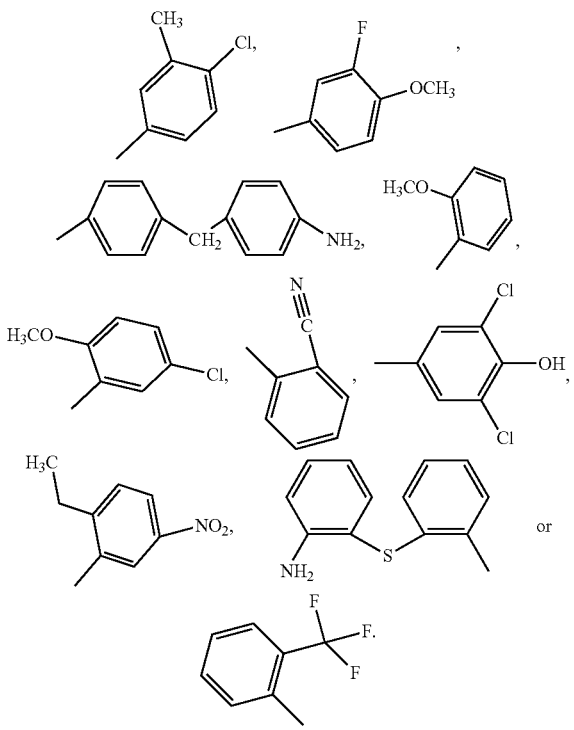

2. An anti-tumor pharmaceutical composition, comprising an aniline-substituted podophyllotoxin-type derivative or a salt thereof as claimed in claim 1 in an effective amount in anti-tumor treatment, and a pharmaceutically acceptable carrier thereof.

3. A method for preparing the aniline-substituted podophyllotoxin-type derivatives as claimed in claim 1, comprising the steps of:
introducing, by aniline substitution reaction, 4-chloro-3-methylaniline, 3-fluoro-4-methoxyaniline, 4,4'-diaminodiphenylmethane, o-anisidine, 4-chloro-2-aminoanisole, o-aminobenzonitrile, 2,6-dichloro-4-aminophenol, N,N-dimethylamino metanil, 2-ethyl-5-nitroaniline, 2,2'-diaminodiphenylsulfide or 2-aminobenzotrifluoride into position 4 of C-ring of podophyllotoxin and 4'-demethylepipodophyllotoxin respectively, to get crude product of aniline-substituted podophyllotoxin-type derivatives.

4. The method as claimed in claim 3, wherein, the aniline reaction comprises: (1) activating position 4 of C-ring of podophyllotoxin or 4'-demethylepipodophyllotoxin; (2) dissolving podophyllotoxin or 4'-demethylepipodophyllotoxin with activated position 4 of C-ring in an organic solvent, then adding 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2,2'-diaminodiphenylsulfide or 2-aminobenzotrifluoride respectively; and (3) stirred to carry out the aniline reaction.

5. The method as claimed in claim 4, wherein, activating position 4 of C-ring of podophyllotoxin and 4'-demethylepipodophyllotoxin is carried out by using hydrobromic acid to activate position 4 of C-ring of podophyllotoxin and 4'-demethylepipodophyllotoxin;
wherein the activating includes steps of:
drying podophyllotoxin and 4'-demethylepipodophyllotoxin, and under protection of nitrogen, adding hydrobromic acid while stirring under an ice-bath; and after the addition, removing from the ice-bath, then reacting under 20-25° C. for 5-12 hours.

6. The method as claimed in claim 4, wherein, the organic solvent in step (2) is methylene chloride; the stirring is carried out in vacuo with rotational speed of 50 to 800 rpm, or 600 rpm; a temperature of the aniline substitution reaction is 10-40° C., and a reaction time of the aniline substitution reaction is 12-48 hours.

7. The method as claimed in claim 3, wherein, in the aniline substitution reaction, a molar ratio between podophyllotoxin or 4'-demethylepipodophyllotoxin and 4-chloro-3-methylaniline, 3-fluoro-4-methoxyaniline, 4,4'-diaminodiphenylmethane, o-aminoanisole, 4-chloro-2-aminoanisole, o-aminobenzonitrile, 2,6-dichloro-4-aminophenol, N,N-dimethylamino metanil, 2-ethyl-5-nitroaniline, 2,2'-diaminodiphenylsulfide or 2-aminobenzotrifluoride is 1:2.

8. The method as claimed in claim 3, further comprising:
(1) subjecting the crude product of aniline-substituted podophyllotoxin-type to rotary evaporation and concentration, then extracting by methylene chloride/water with volume ratio of 1:1 three times, to get a sample to be separated and purified;
(2) separating the sample to be separated and purified by silica gel column chromatography, gel column chromatography and high performance preparative liquid chromatography separations sequentially, to obtain a product of compound of formula (V).

9. The method as claimed in claim 8,
wherein the separation by silica gel column chromatography comprises: (1) conducting normal phase silica gel column chromatography, wherein normal phase silica gel is mixed in organic solvent with low polarity, loaded into column, and balanced with eluent which is formed from chloroform and acetone with volume ratio of 10:1; (2) dissolving samples with the eluent, subjecting to sample adsorption, then eluting with eluent which is collected later, then evaporating the sample to dryness and recrystallizing,
wherein the separation method by gel column chromatography comprises: (1) soaking the gel with eluent which is formed from petroleum ether, chloroform and methanol with volume ratio of 5:5:1 in order; loading processed gel into column and balancing with the eluent; (2) dissolving the sample preliminary separated by silica gel column chromatography in the eluent, subjecting to sample absorption, and then eluting with eluent which is collected later, then evaporating the sample to dryness and recrystallizing.

* * * * *